(12) United States Patent
Virkus et al.

(10) Patent No.: US 8,317,736 B2
(45) Date of Patent: Nov. 27, 2012

(54) COMPRESSION OR SUPPORT STOCKING

(75) Inventors: Antje Virkus, Strasbourg (FR); Erik Berndt, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 641 days.

(21) Appl. No.: 12/308,992

(22) PCT Filed: Apr. 14, 2007

(86) PCT No.: PCT/EP2007/003314
§ 371 (c)(1),
(2), (4) Date: Nov. 10, 2009

(87) PCT Pub. No.: WO2008/003361
PCT Pub. Date: Jan. 10, 2008

(65) Prior Publication Data
US 2010/0137776 A1 Jun. 3, 2010

(30) Foreign Application Priority Data
Jul. 7, 2006 (DE) .................. 10 2006 032 223

(51) Int. Cl.
*A61F 13/00* (2006.01)
*A43B 17/00* (2006.01)
(52) U.S. Cl. .......... 602/63; 602/60; 602/61; 602/62; 2/240
(58) Field of Classification Search .......... 602/60–64; 2/239–242, 409, 61; 66/178 A, 178 R, 172 E, 66/190
See application file for complete search history.

(56) References Cited

U.S. PATENT DOCUMENTS

| | | | |
|---|---|---|---|
| 3,392,553 A | 7/1968 | Burleson | |
| 4,502,301 A * | 3/1985 | Swallow et al. | 66/178 A |
| 5,005,567 A | 4/1991 | Gilman | |
| 6,216,495 B1 | 4/2001 | Couzan | |
| 6,613,007 B1 | 9/2003 | Reid | |
| 6,684,412 B2 | 2/2004 | Ricci | |
| 2002/0172781 A1 | 11/2002 | Ricci | |
| 2005/0015854 A1 | 1/2005 | Eisenberg | |
| 2005/0267393 A1 | 12/2005 | Gardon-Mollard | |
| 2007/0021704 A1* | 1/2007 | Hariri et al. | 602/48 |

FOREIGN PATENT DOCUMENTS

| | | |
|---|---|---|
| DE | 36 31 022 | 3/1987 |
| DE | 42 16 650 | 8/1993 |
| DE | 199 46 019 | 3/2001 |
| DE | 600 01 707 | 3/2004 |
| DE | 699 17 456 | 5/2005 |
| EP | 0 621 024 | 10/1994 |
| FR | 2 762 780 | 11/1998 |
| FR | 2 774 281 | 8/1999 |
| FR | 2 780 637 | 1/2000 |
| JP | 49 072431 | 10/1947 |
| WO | WO 01/00118 | 1/2001 |

* cited by examiner

*Primary Examiner* — Kim M Lewis
(74) *Attorney, Agent, or Firm* — Paul Vincent

(57) ABSTRACT

A compression or support stocking encases a human leg. The stocking has a first understocking and a first overstocking, each with a leg section and a foot section, which can be worn over each other, wherein the understocking has a continuous pressure progression in the area between measuring points B and B1, and the pressure at measuring point B1 amounts to 90%-100% of the pressure at measuring point B. The compression or support stocking can be used for treating Ulcus cruris venosum.

15 Claims, 4 Drawing Sheets

COMPRESSION OR SUPPORT STOCKING

This application is the national stage of PCT/EP2007/003314 filed on Apr. 14, 2007 and claims Paris Convention Priority to DE 10 2006 032 223.1 filed Jul. 7, 2006.

BACKGROUND OF THE INVENTION

The invention concerns a compression or support stocking to encase a human leg, comprising a first understocking and a first overstocking, each with a leg section, which can be worn over each other, wherein the overstocking is permanently or only temporarily worn over the understocking.

Compression and support stockings are used in medical compression therapy and also in the non-therapeutic cosmetic area as support stockings to apply resting and also working pressure to a human leg. Resting pressure in this context refers to the pressure that the stocking as such applies to the resting leg, whereas working pressure is the pressure that is exerted on the leg through muscle contraction and by the stocking while the leg is being moved.

In this context, it is also common, in addition to pure compression therapy for treating a number of venous diseases, to treat illnesses where compression pressure is to be applied in addition to wound dressing. For this purpose, a wound dressing is first applied to a wound and a compression stocking is then pulled over it.

A method for treatment of such diseases is known, for example, from U.S. Pat. No. 5,005,567, where an easily applicable loosely-knit sock is first pulled over the wound dressing material and then an elastic sock with a low coefficient of friction is pulled over the first understocking between stockings, with the application of the second stocking being facilitated due to the low friction between the stockings.

The above-mentioned method envisions that the understocking has no compressive effect whatsoever. The overstocking can have a compression ranging from 10 through 50 mm mercury in the ankle area.

The disadvantage of that system is that the overstocking must have high compression power as all compression is to be achieved by the overstocking. Furthermore, there is the danger of wrinkling in the area of the understocking as the understocking is loosely applied.

In addition, DE 42 16 650 A1 provides a cosmetic support stocking for treating cosmetically relevant orange-peel skin and improving the physiological muscular pump, consisting of several compression stockings or compression pantyhose or bandages that are to be worn over each other. Furthermore, the individual parts can be firmly or flexibly joined with each other to secure their positions relative to each other.

Each individual stocking has only a low compressive effect and can thus be easily and quickly applied. Pulling several stockings over each other, however, considerably increases the pressure exerted on the skin, so that a sufficient compression pressure is eventually achieved.

Finally, a multilayer compression stocking system is known from WO 01/00118 A1, which envisions markings for the positioning of the stockings relative to each other to ensure that the compression pressure is distributed correctly on a leg.

Furthermore, a number of monolayer compression stockings are known.

Norm RAL-GZ 387 of September 2000 governs the measuring and quality assurance of medical compression stockings. The testing provisions of the norm describe how the pressure of a compression stocking on a leg is to be determined.

The invention is based on the task of providing a generic compression or support stocking to encase a human leg which can be used favorably to treat chronic venous insufficiency as well as its signs, symptoms and complications such as, for example, Ulcus cruris venosum, while ensuring easy application.

SUMMARY OF THE INVENTION

The invention fulfills this task by means of a compression or support stocking according to the elements recited in the independent claims, wherein the understocking has a continuous pressure progression in the area between measuring points B and B1, and the pressure at measuring point B1 amounts to 90% to 100% of the pressure at measuring point B.

Measuring points B and B1 are points relating to the ankle area of a human leg and enclosing that area between them. The measuring points are determined in accordance with the pertinent provision RAL-GZ 387. In the context of the present invention, continuous pressure progression between measuring points B and B1 means a pressure progression whose interpolated single values at every point between points B and B1 deviate from the value measured at B by a maximum of 10%, in particular by a maximum of 7% and very particularly by a maximum of 5%. A continuous pressure progression between other measuring points must correspond to the present provision accordingly.

In this context, measuring point B corresponds to a point on the human lower leg located immediately above the ankle at the point where the lower leg has the lowest circumference. Measuring point B1 corresponds to a point on the human lower leg located at the given distance above measuring point B, i.e. proximally at the transition from the Achilles tendon to the calf. Other points under the RAL Norm (RAL-GZ 387) are, for example, point C, i.e. the highest circumference of the calf, and point D, which is located two fingers below the hollow of the knee.

The invention envisions that the pressure at measuring point B1 in the understocking amounts to between 90% and 100% of the pressure at measuring point B. Preferably, the pressure at measuring point B is equal to the pressure at measuring point B1. The invention envisions that the area between measuring points B and B1 is a therapeutic area in particular for treating complications of chronic venous insufficiency such as, for example, Ulcus cruris venosum, which is known as "gaiter leg ulcer" in its most severe form, where the patient has open lesions of the skin in the ankle area. These lesions are then covered with wound dressings for treatment, which are subsequently covered by the understocking. Providing an essentially continuous pressure progression with a maximum deviation of 10% in the ankle area ensures that a constant pressure is built up across the entire area to be treated, so that the skin surface to be treated is not weighted with different pressures.

The present invention therefore also concerns use of a compression or support stocking to encase a human leg, comprising a first understocking and a first overstocking, each with a leg section and a foot section, which can be worn over each other, wherein the understocking has a continuous pressure progression in the area between measuring points B and B1, and the pressure at measuring point B1 amounts to 90%-100% of the pressure at measuring point B, to produce a preparation for treating chronic venous insufficiency as well as its signs, symptoms and complications, in particular healed or florid Ulcus cruris venosum, dermatoliposclerosis and/or atrophie blanche.

According to Widmer, chronic venous insufficiency can, in principle, be classified into three stages. Based on this system, chronic venous insufficiency is classified as follows: Grade I of chronic venous insufficiency is characterized by starburst-like veins (Corona phlebectatica) located around the ankle and above the vault of the foot and by ankle edema.

Grade II manifests itself in hyperpigmentation of the skin, lower leg edema and dermatoliposclerosis. The skin is firmly interwoven with the crural fascia, cannot be lifted in creases and is excessively shiny. An extreme variation of dermatoliposclerosis is atrophie blanche (also referred to as Capillaritis alba), which occurs almost exclusively as a complication of chronic venous insufficiency and manifests itself by depigmentation in the distal lower leg as a result of vasculitis of small skin vessels that is often a painful precursor of Ulcus cruris. This skin change typically shows white, atrophic, coin- to palm-sized foci. They are commonly located in the ankle region or in the scarred areas of healed ulceration.

Grade III manifests itself as florid or healed Ulcus cruris venosum. Its predilection site is the perimalleolar region (Bisgaard's link), but it can also occur at other locations on the lower leg. Extensive ulcers affecting the entire lower leg in circular shape are referred to as "gaiter leg ulcer". Another classification of chronic venous insufficiency that is common today is the CEAP classification. In this context, see the publication "Grundlagen der Phlebologie", chapter 4.3 "Chronische Venöse Insuffizienz" (ed. R. Rabe, $3^{rd}$ edition, pp. 111-129).

In particular, the overstocking and/or the understocking of a compression or support stocking according to the invention may be provided as knit, preferably circular knit, fabric. In particular, the stockings are manufactured as so-called AD stockings in accordance with RAL-GZ 387. The stockings can also be manufactured according to the specifications (Cahier des charges) described in the "Referentiel technique des ortheses elastiques de contention des membres" (Revision No. 05). Such stockings can generally have an optional toe section and a foot section with a heel, an adjoined leg section in the area of the lower leg and a stocking with a stocking top.

In a preferred embodiment, the pressure of the understocking at measuring point B1 amounts to between 93% and 100%, in particular 95% through 100% and in particular 98% through 100% of the pressure at measuring point B. A pressure progression that is as continuous as possible improves the wound healing and the fixation of the wound dressing under the understocking. Furthermore, one embodiment of the invention envisions that the overstocking has a continuously degressive or gradually degressive pressure progression starting from measuring point B and progressing towards the hip of the human leg, i.e. in proximal direction. In particular, the overstocking may be a compression stocking with a pressure progression in accordance with the norm RAL-GZ 387.

The RAL Norm (RAL-GZ 387) stipulates different compression classes, wherein the overstocking can be a stocking with compression classes 1 through 4 under the norm.

The understocking can in particular be a stocking whose pressure progression does not correspond to the RAL Norm, but also stockings in accordance with the norm can be provided. The understocking shows a degressive progression taking a continuously or gradually degressive course or a continuous or constant pressure progression in the area proximal of measuring point B1. In an embodiment where the understocking has a continuous pressure progression in the area proximal of measuring point B1 or proximal of the area to be treated, this embodiment may in particular provide merely a lower compression pressure under 8 mm Hg in the understocking. Wrinkling under the overstocking when putting the overstocking on must nevertheless be prevented.

In this context, the invention envisions in particular that the understocking is responsible for providing the desired resting and working pressures, while the overstocking also contributes to this. Therefore, in a particularly favorable embodiment, the understocking is worn day and night to fix the wound dressing firmly on the wound to be treated and prevent too frequent removal of the wound dressing from the wound, which affects the wound healing process. At the same time, however, this ensures that at the time of night's rest, during which the legs are normally put up, the compression effect is only weak, so that numbness sensation and strangulation in the area of the legs are avoided. In the course of the day, during which the wearer of the compression stocking moves around, the overstocking, which provides a stronger compression effect, can then be pulled over the understocking in addition without interfering with the wound healing process, so that during the day, in addition to the existing resting and working pressures exerted by the understocking, a similar, stronger resting and working pressure is achieved with the help of the overstocking, so that the muscular activity results in additional compression therapy and the underlying disease is positively influenced. The provision of two stockings placed over each other enables a lower compression effect for each stocking, which facilitates the process of putting the stockings on.

In one embodiment, the joint compression pressure of overstocking and understocking may be 5 through 15 mm mercury (mm Hg) higher than the compression pressure of the individual stockings. The compression pressure is measured by means of a compression testing device according to the Hohenstein system (Nosy), a detailed description of which can be read in the "Hohensteiner Forschungsbericht" of January 1982 and "Phlebol and Proktol." 11: 34-41 (1982).

One embodiment envisions that the joint compression at point B of both stockings is between 34 and 60 mm Hg, preferably between 34 and 50 mm Hg, with one mm Hg equaling 133.322 pascal.

The understocking has a compression of 15 through 32 mm Hg, preferably of 15 through 25 mm Hg, at measuring point B. The value at point B1 amounts to 90% to 100% of the value at point B. Values from 5% to 80%, preferably between 50% and 80% or 5% to 50%, of the pressure at point B can occur at a point C, with the pressure drop occurring between B1 and C.

The overstocking, which is manufactured in accordance with the RAL Norm (RAL-GZ 387), has a compression of 15 to 32 mm Hg at point B.

An embodiment may provide a working pressure, which is caused on a leg by wearing a compression or support stocking according to the invention, which is at least 10 to 35 mm Hg higher than the resting pressure, with the resting pressure amounting to at least 34 mm Hg.

In particular, the compression stockings according to the invention may be circular knit compression stockings, which are, in particular, so-called AD stockings, i.e. calf stockings in accordance with the RAL Norm (RAL-GZ 387). One embodiment envisions that the compression stockings are manufactured according to the specifications (Cahier des charges) described in the "Referentiel technique des ortheses elastiques de contention des membres" (Revision No. 05).

Furthermore, to facilitate the application of the overstocking over the understocking, one embodiment may have a foot section that is integrally formed at the understocking and has a dynamic coefficient of friction of $\mu_D \leq 0.65$, in particular $\mu_D \leq 0.60$ and very particularly preferably $\mu_D \leq 0.55$, wherein the coefficient of friction is measured analogous with DIN-EN-ISO 8295: 2004-10. This includes measuring the material of the integrally formed foot section to be analyzed against the material that is located at the interior of an overstocking in a situation where the stocking has been correctly applied, namely the surface (mating material) which is to be pulled over the foot section according to the application requirements. The materials are analyzed in an unstreched condition while ensuring that all materials lie uncreased, that the materials are measured along manufacturing direction and that the mating material is clamped along the manufacturing direction. Otherwise, the conditions of the norm referenced above apply, wherein in particular a testing speed of 100 mm/min is to be observed.

The foot section of the understocking may provide an integrally knit toe section as well as an integrally formed heel, with the heel having in particular no stitched seam but being developed only through thermal deformation of the fabric. The foot section has preferably no compression, with the very smooth fabric ensuring easy application of the overstocking in the strongly bent foot area.

The overstocking and/or the understocking may have a so-called reciprocated heel, which corresponds to RAL Norm RAL-GZ 387, wherein the toe area may be open or closed.

In particular, the understocking and/or the overstocking may also have a pressure relief area bordering the leg section. If the stocking or the stockings have been applied correctly, this pressure relief area is located in the ankle area and between the leg section and the foot section of the stocking accordingly. This pressure relief area has the advantage that the transition from very high pressure to low through very low pressure is not abrupt in the area bordering the ankle area, in particular at point B, which shows the highest pressure, and that no constriction thereby occurs within the area covered by the stocking. In a particularly preferred embodiment, understocking and/or overstocking has a reciprocated heel, wherein a pressure relief area is located in the border area of the reciprocated heel. In particular, this pressure relief area may be upsilon-shaped (Y-shaped) in a lateral view of the stocking. In that embodiment, the reciprocated heel is completely encircled by the pressure relief area. Another embodiment envisions, however, that the pressure relief area is located radially at the end of the leg section in the understocking and/or overstocking.

Furthermore, another embodiment may be provided with a pattern, in particular a wave pattern, in the leg section of the understocking and/or the overstocking, with the waves running in circumferential direction. This wave pattern may in particular be knit into the material, so as to form raised and less raised zones. This pattern can help achieve better fixation of both stockings over each other, as it increases the roughness and thus the adhesion of both leg sections. In a particularly preferred embodiment, the patterns of understocking and overstocking are congruent when the stockings are worn over each other.

It is also favorable for the understocking to have a marking for the positioning of the overstocking. This marking may in particular consist of the top edge of the understocking. Furthermore, the marking may consist of a change of color, texture or pattern in the understocking, with the top edge of the leg section or the top of the overstocking being pulled up to that marking.

In a preferred embodiment, the knit fabric of the stockings contains at least one elastic insertion thread and at least one elastic knitting thread to achieve the desired elastic properties.

In a particularly preferred embodiment, the understocking and/or the overstocking is made of threads consisting of an elastic core thread that is enwound with yarn containing cotton fibers, in particular a staple fiber yarn, as enwinding thread, at least in the leg section. A particularly favorable embodiment envisions that an elastane core, for example a core made of Lycra®, is used as the core thread, with the core being enwound with a single, double or multiple layer of thread and the yarn material used to enwind the core being a multifilament yarn made of polyamide or either a multifilament yarn made of polyamide or a staple fiber yarn being used as the enwinding thread.

It is favorable if the staple fiber yarn is made of 70% through 90% cotton and 10% through 30% algae containing cellulose material. The cellulose threads containing algae material may in particular be Seacell® fibers (SeaCell GmbH, Rudolstadt, Germany), wherein the algae materials are incorporated in the cellulose fibers. The algae are evenly spread within the cellulose fibers in particle form.

The algae particles may come from brown algae, namely preferably *Ascophyllum nodosum*, or red algae, namely preferably *Lithothamnium calcareum*. The fibers can be produced using the Lyocell method. Using such fibers has the advantage that agents such as vitamin E (tocopherols), carotenoids and minerals in their ionic form, such as sodium ions, calcium ions or magnesium ions, are released in the presence of water and/or perspiration. The agents are incorporated in the algae containing fibers for longer periods and do not immediately wash out even during laundering operations. Seacell® or other algae containing fibers consist of at least 90% w/w cellulose, 0.1-10% w/w algae and 0-10% other additives. When released, the agents contained in the algae have a positive effect on the wearer's skin. Provided that both the understocking and the overstocking contain algae material, this prevents a gradient of agents between the stockings and thus supports the release of the agents onto the wearer's skin.

The present invention therefore also concerns the use of a compression or support stocking to encase a human leg, in particular comprising a first understocking and a first overstocking, each with a leg section and a foot section, which can be worn over each other, wherein in particular the understocking has a continuous pressure progression in the area between measuring points B and B1, and the pressure at measuring point B1 amounts to 90%-100% of the pressure at measuring point B, wherein the stocking, in particular the understocking, comprises staple fibers comprising algae containing cellulose material to produce a preparation for treating dermatoliposcierosis or atrophie blanche.

Furthermore, the invention concerns the use of a compression or support stocking according to one of the previous claims for treating Ulcus cruris venosum by placing a wound dressing on a skin lesion and covering the wound dressing with the understocking and wearing the overstocking at least temporarily, preferably at daytime, over the understocking.

In accordance with a further aspect, the present invention also concerns a set consisting of a compression or support stocking to encase a human leg and a wound dressing, wherein the compression or support stocking comprises a first understocking with a leg section and a foot section, wherein the understocking has a continuous pressure progression in the area between measuring points B and B1, and the pressure at measuring point B1 amounts to 90%-100% of the pressure at measuring point B. Wound dressings which have foam material, in particular a polyurethane foam, as a wound contact layer are particularly preferred. This wound contact layer may be applied to a carrying layer, which is, in turn, adhesive. In a preferred embodiment, the compression or support stocking may additionally comprise a first overstocking with a leg section and a foot section, which can in particular be worn over the understocking.

The invention is explained in more detail below on the basis of a drawing, wherein:

DESCRIPTION OF THE PREFERRED EMBODIMENT

Figure 1:
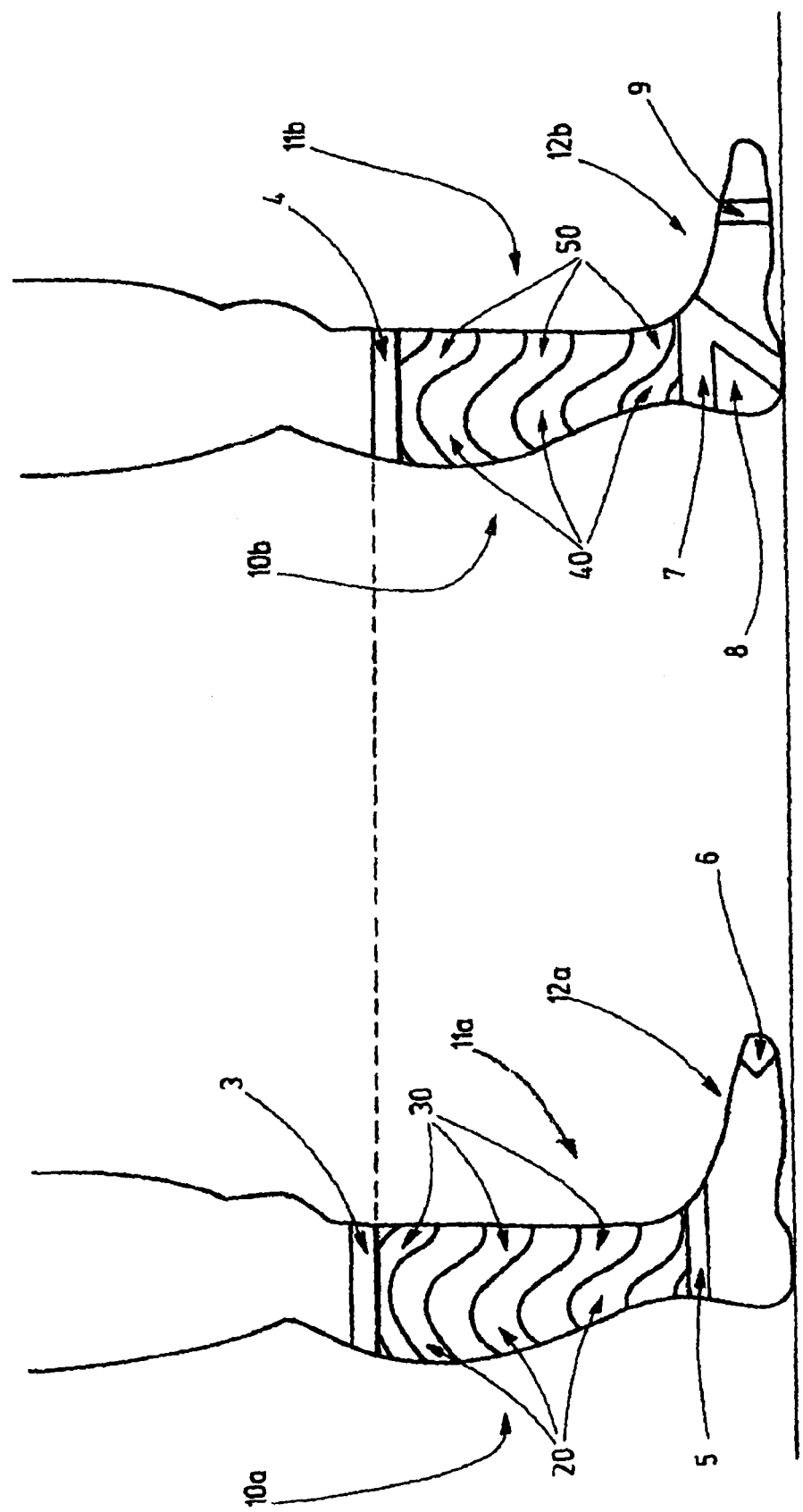
FIG. 1 shows a compression stocking according to the invention.

FIG. 1 shows the structure of a compression stocking 10 according to the invention. This compression stocking is manufactured as a knee-high stocking or AD stocking consisting of an understocking 10a and an overstocking 10b, each with a leg section 11a, 11b, and each with a foot section 12a, 12b, which can be applied and worn over each other. To clarify the component parts of each stocking, FIG. 1 shows the understocking 10a and the overstocking 10b separately on the same leg. When used, these stockings are put on or worn over each other in such a way that the top edge of the stocking top 4 of the overstocking corresponds to the bottom edge of the stocking top 3 of the understocking (shown by the dotted line in FIG. 1).

The understocking 10a has a pressure relief area 5 at the top end of the foot section 12a, bordering the leg section 11a. This pressure relief area 5 is integrally and seamlessly formed at the foot section 12a and integrally and seamlessly formed at the leg section 11a. The foot section 12a of the understocking 10a is shown with a closed toe 6, with this toe being made of reinforced material in comparison to the rest of the foot section.

The overstocking 10b also has a pressure relief area 7. This relief area 7 completely encloses a reciprocated heel 8 provided here and is integrally and seamlessly formed at a leg section 11a and integrally and seamlessly formed at the reciprocated heel 8. The pressure relief area is V-shaped as shown here or Y-shaped (not shown) in the lateral view, depending on the size of the heel. The foot section 12b of overstocking 10b is shown with an open toe, wherein the foot section has a stocking top 9 at its end.

Figure 2:
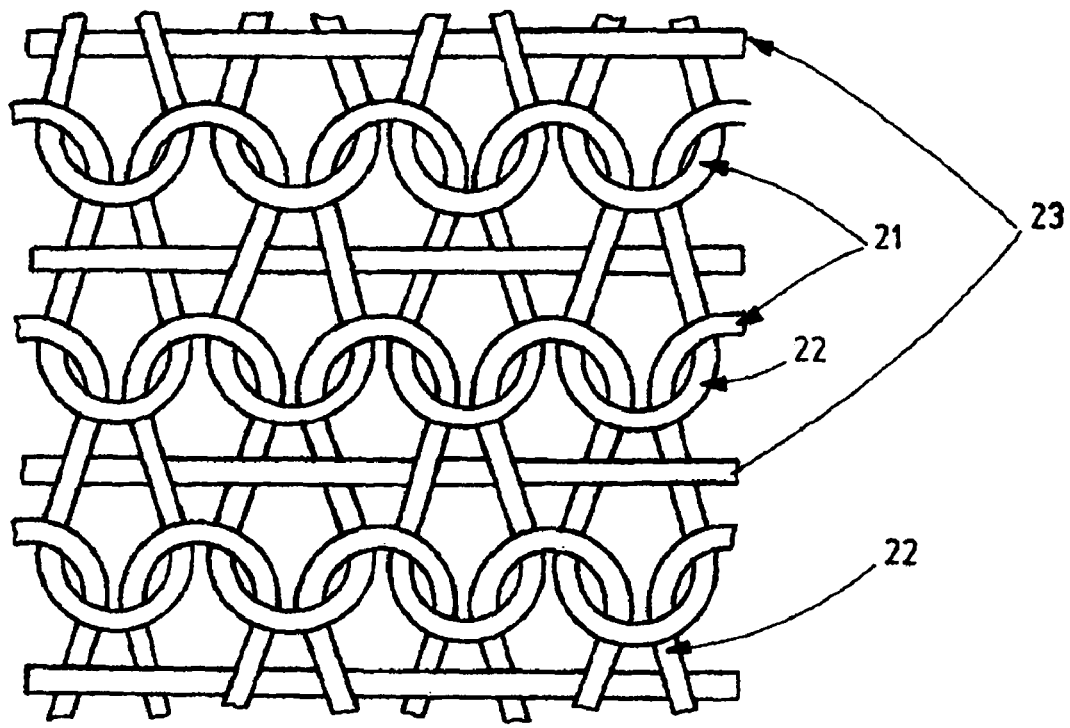
FIG. 2 shows a laying pattern of a part of a leg section of an understocking.
Figure 3:
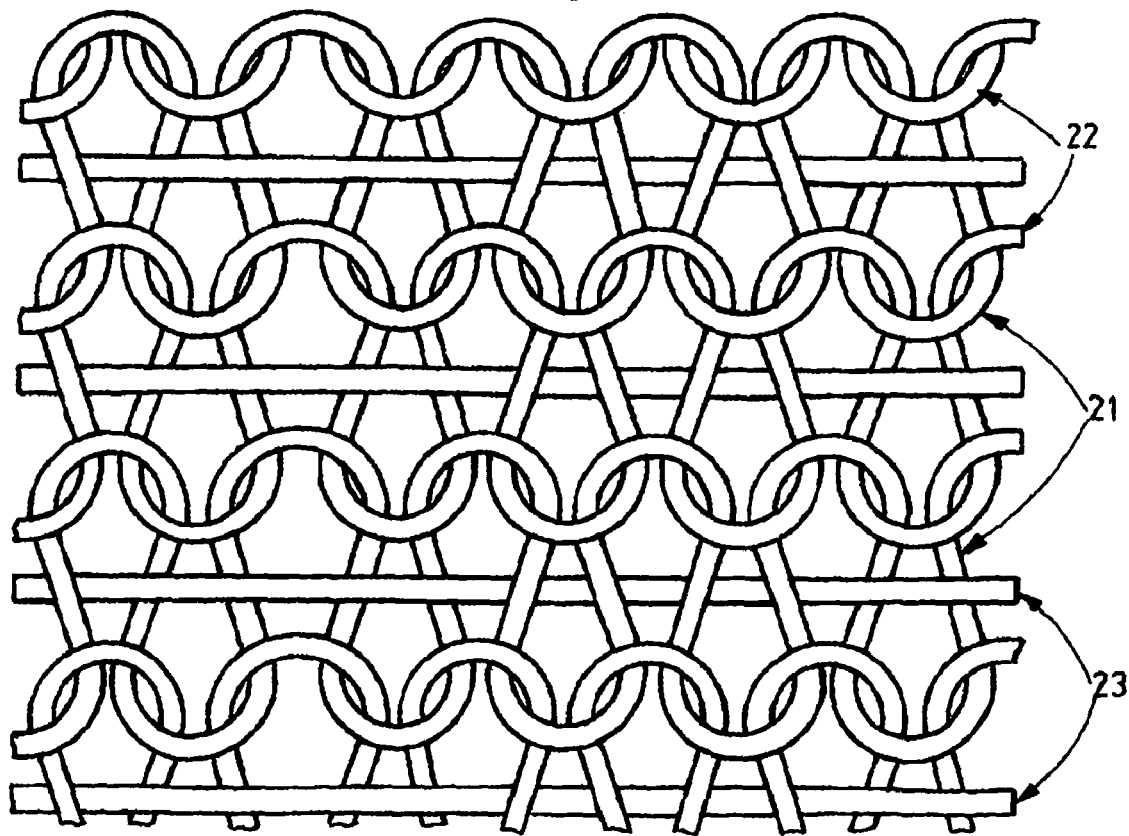
FIG. 3 shows a laying pattern of another part of a leg section of the understocking.

Both the understocking 10a and the overstocking 10b are shown as circular knit fabric, wherein each stocking has a wave pattern in its respective leg section 11a, 11b. This wave pattern is enabled by different types of knitting, with two different knits being used. The wave pattern is designed in a way that the two knitting types follow each other in turns. The knitting pattern of the understocking 10a in the leg section 11a is shown in the laying patterns in FIG. 2 and FIG. 3. FIG. 2 shows the laying pattern of the areas 20 (FIG. 1). Accordingly, two different knitting threads 21, 22 and an insertion thread 23 are used in these areas. The understocking has a 1:1 insertion thread and alternating knitting threads. FIG. 3 illustrates the knit of the areas 30 (see FIG. 1). Accordingly, the same knitting threads 21, 22 (compared with FIG. 2) and the same insertion thread 23 are used in these areas. In contrast to the areas 20, however, the insertion thread is used as a 2:2 insertion thread in the areas 30.

Both the pressure relief area 5 of the understocking and the pressure relief area 7 of the overstocking are manufactured using the same materials as the respective leg sections 11a, 11b of the two stockings. In these areas, the insertion thread is used as a 3:2 insertion thread.

The laying patterns of the corresponding areas 40 and 50 in the overstocking 10b correspond to the laying patterns illustrated in FIGS. 2 and 3, with the difference being that only one knitting thread and one insertion thread are used in the entire leg section 11b of the overstocking (not shown here).

The following example specifies the materials for understocking and overstocking. The numbering refers to FIGS. 1, 2 and 3.

Materials Overstocking 10b:
Knitting threads stocking top 4:
a) 44 dtex EL Lycra® (core)—enwound with a double layer of
i) 44f26/1 dtex PA 6.6 (Tactel® diabolo)
b) 78 dtex EL Lycra® (core)—enwound with a double layer of
i) 26f28/1 dtex PA 6.6 (microfiber yarn)
Knitting thread 41 in leg 11b, foot 12b and pressure relief area 7:
a) 44 dtex EL Lycra® (core)—enwound with a double layer of
i) 44f26/1 dtex PA 6.6 (Tactel® diabolo)
Insertion thread 42 in leg 11b, foot 12b and pressure relief area 7:
a) 570 dtex EL Lycra® (core)—enwound with a double layer of
i) 44f13/1 dtex PA 6.6 and
ii) staple fiber yarn Nm170/1
Knitting thread heel 8 and stocking top 9 (open toe):
a) 78 dtex EL Lycra® (core)—enwound with a double layer of
i) 60f68/1 dtex PA 6.6 (microfiber yarn)
Materials Understocking 10a:
Knitting thread stocking top 3:
a) 78 dtex EL Lycra® (core)—enwound with a double layer of
i) 26f28/1 dtex PA 6.6 (microfiber yarn)
Knitting thread 21, 22 in leg 11a and pressure relief area 5:
a) 44 dtex EL Lycra® (core)—enwound with a double layer of
i) 44f26/1 dtex PA 6.6 (Tactel® diabolo)
b) 44 dtex EL Lycra® (core)—enwound with a double layer of
i) 44f34/1 dtex PA 6.6 and
ii) staple fiber yarn Nm170/1
Insertion thread 24 in leg 11a and pressure relief area 5:
a) 156 dtex EL Lycra® (core)—enwound with a double layer of
i) 44f13/1 dtex PA 6.6 and
ii) staple fiber yarn Nm170/1
Knitting thread in foot 12a:
a) 78f51/1 dtex Tactel® PA 6.6
b) 44 dtex EL Lycra® (core)—enwound with a double layer of
i) 44f26/1 dtex PA 6.6 (Tactel® diabolo)
Knitting thread toe 6:
a) 78 dtex EL Lycra® (core)—enwound with a double layer of
i) 26f28/1 dtex PA 6.6 (microfibers)

EL refers to elastane and Nm to "Nummer metrisch" (metric number). Furthermore, an elastane core enwound with a double layer is enwound with a first yarn i) as a first layer and with a second yarn ii) as a second layer or with the first yarn i) as a second layer over the first layer, with the threads intersecting. The yarn supplier for the enwound yarns is the company Zimmermann, Weiler Simmerberg, Germany. The staple fiber yarn has the following composition: 75% cotton, 25% Seacell®, Seacell® contains 8% through 12% algae incorporated in cellulose. The yarn is supplied by SeaCell GmbH, Rudolstadt, Germany.

Figure 4:
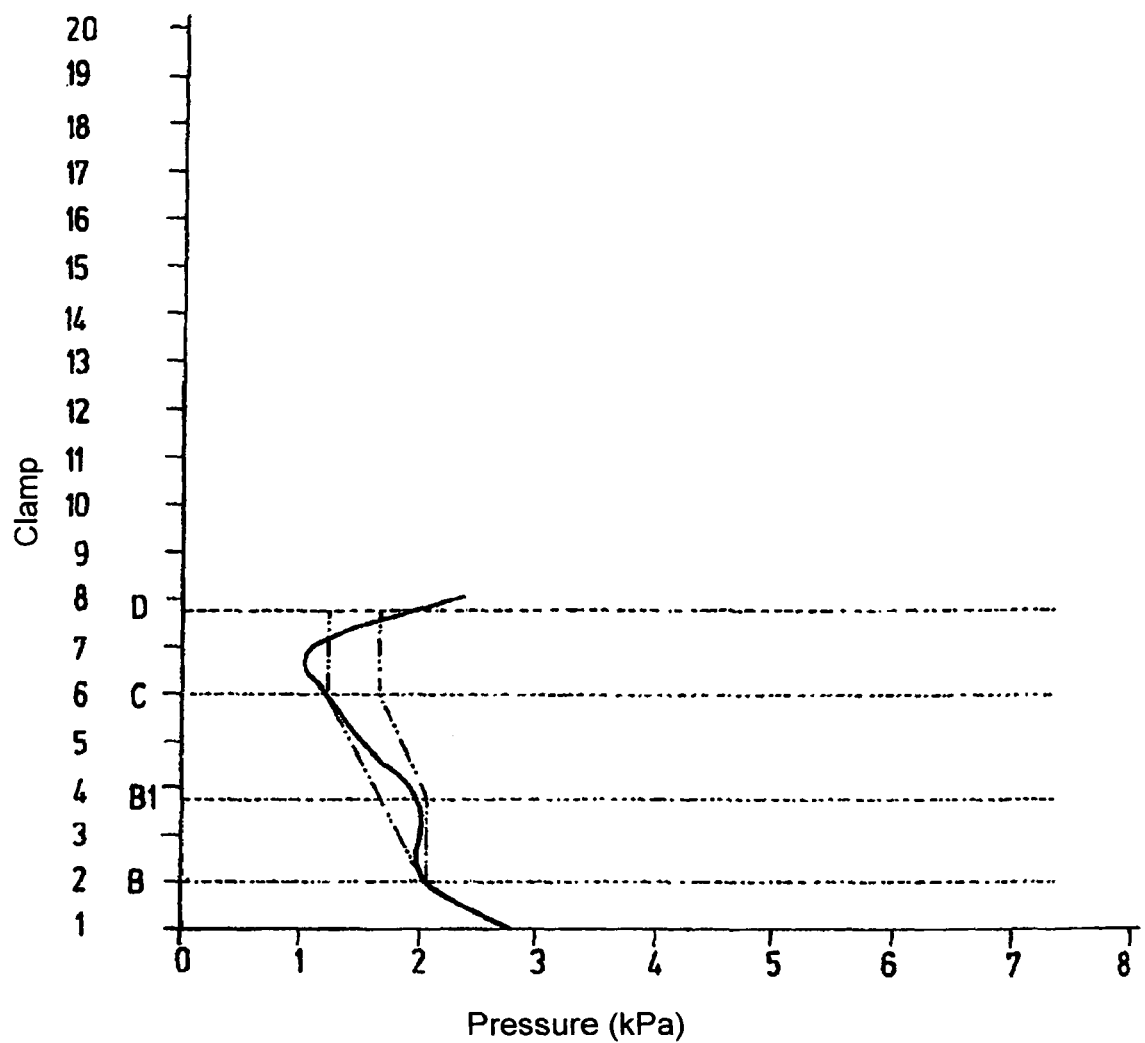
FIGS. 4 and 5 show the measured pressure curves of a compression stocking according to the invention.
Figure 5:
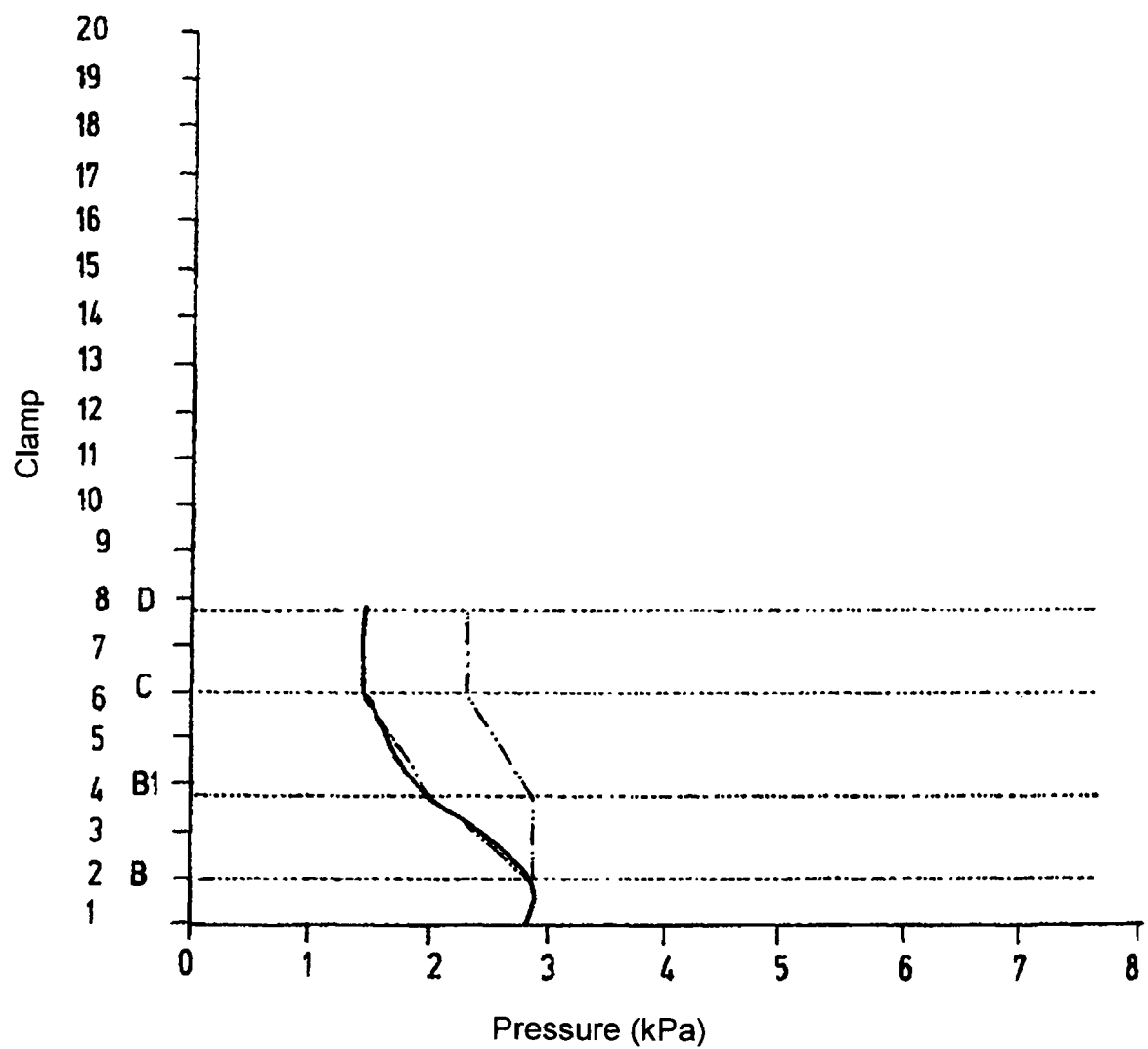

In addition, FIGS. 4 and 5 below show pressure progression for the overstocking and the understocking. The measuring of compression and fitting of the clamps is carried out according to RAL-GZ 387, wherein the understocking (FIG. 4) has a largely constant compression pressure in the area between B and B1 after a slight initial pressure drop. The double dotted lines define the admissible area according to the RAL Norm (RAL-GZ 387). As can be seen here, the understocking is not a stocking as defined by the RAL Norm (RAL-GZ 387), as it leaves the stipulated area between measuring points C and D. The depiction of the overstocking (FIG. 5), however, shows that this stocking essentially corresponds to the pressure progression stipulated for a norm stocking under the RAL Norm (RAL-GZ 387). The compression pressure is measured by means of a compression testing device using the Hohenstein system (Nosy), a detailed description of which can be read in the "Hohensteiner Forschungsbericht" of January 1982 and "Phlebol and Proktol." 11: 34-41 (1982).

Other advantages and properties of the invention are described in the other application documents.

A compression stocking or support stocking can be provided in the above-mentioned way, which is very well suited to be used for treating diseases where open wounds and skin lesions must be covered by a wound dressing within the compression area.

We claim:

1. A compression or support stocking to encase a human leg, the stocking comprising:
    an understocking having an understocking leg section and an understocking foot section, said understocking leg section having a first wavy pattern travelling in a circumferential direction, said first wavy pattern defining first raised zones; and
    an overstocking having an overstocking leg section and an overstocking foot section, said overstocking leg section having a second wavy pattern travelling in a circumferential direction, said second wavy pattern defining second raised zones, wherein said first and said second wavy patterns are congruent when said overstocking and said understocking are worn over each other, said understocking having a continuous pressure progression in an area between a first measuring point and a second measuring point, wherein a pressure at said first measuring point amounts to 90%-100% of a pressure at said second measuring point.

2. The compression or support stocking of claim 1, wherein said understocking and said overstocking are knit or circular knit fabric.

3. The compression or support stocking of claim 1, wherein said pressure at said first measuring point of said understocking corresponds to between 93% and 100% of said pressure at said second measuring point.

4. The compression or support stocking of claim 1, wherein said overstocking has a continuously degressive or gradually degressive pressure progression starting from said second measuring point and progressing towards a hip of the human leg.

5. The compression or support stocking of claim 1, wherein said overstocking is a compression stocking with a pressure progression in accordance with RAL-GZ 387.

6. The compression or support stocking of claim 1, wherein said understocking has a continuously degressive or gradually degressive pressure progression in an area proximal said first measuring point.

7. The compression or support stocking of claim 1, wherein a joint compression pressure of said overstocking and said understocking is 5-15 mm Hg higher than a compression pressure of an individual stocking.

8. The compression or support stocking of claim 1, wherein said understocking has an integrally formed foot section with a coefficient of friction of $\mu_D \leq 0.65$.

9. The compression or support stocking of claim 1, wherein said understocking has a marking for positioning of said overstocking.

10. The compression or support stocking of claim 9, wherein said marking consists of a change of color, texture or pattern in said understocking.

11. The compression or support stocking of claim 1, wherein said foot section of said understocking has an integrally formed heel section developed through thermal treatment.

12. The compression or support stocking of claim 1, wherein said understocking and/or said overstocking comprises thread or comprises threads in said leg sections, wherein an elastic core thread is enwound with a cotton fiber containing yarn or a staple fiber yarn.

13. The compression or support stocking of claim 12, wherein said cotton fiber containing yarn contains 70%-90% cotton and 10-13% algae containing fibers.

14. Use of a compression or support stocking for treating Ulcus cruris, the compression or support stocking thereby encasing a human leg, the stocking comprising an understocking having an understocking leg section and an understocking foot section, said understocking leg section having a first wavy pattern travelling in a circumferential direction, said first wavy pattern defining first raised zones, and an overstocking having an overstocking leg section and an overstocking foot section, said overstocking leg section having a second wavy pattern travelling in a circumferential direction, said second wavy pattern defining second raised zones, wherein said first and said second wavy patterns are congruent when said overstocking and said understocking are worn over each other, said understocking having a continuous pressure progression in an area between a first measuring point and a second measuring point, a pressure at said first measuring point amounting to 90%-100% of a pressure at said second measuring point, wherein a wound dressing is placed on a skin lesion and covered by said understocking, said overstocking being worn at least temporarily, or at daytime, over said understocking.

15. A compression or support stocking to encase a human leg, the stocking comprising:
    an understocking having an understocking foot section structured to cover a foot region of the leg and an understocking leg section adjacent to said understocking foot section and extending upward from said understocking foot section, said understocking leg section structured to cover a lower leg region of the leg, said understocking leg section having a first wavy pattern travelling in a circumferential direction, said first wavy pattern defining first raised zones; and
    an overstocking having an overstocking foot section covering said understocking foot section and an overstocking leg section covering said understocking leg section, said overstocking leg section having a second wavy pattern travelling in a circumferential direction, said second wavy pattern defining second raised zones, wherein said first and said second wavy patterns are congruent, said understocking having a continuous pressure progression in an area between a first measuring point and a second measuring point, wherein a pressure at said first measuring point amounts to 90%-100% of a pressure at said second measuring point.

* * * * *